(12) United States Patent
Corne et al.

(10) Patent No.: US 11,213,487 B2
(45) Date of Patent: Jan. 4, 2022

(54) NEGATIVELY CHARGED SELF-ASSEMBLING SUPPORTED LIPID BILAYER ON MESOPOROUS SILICA NANOPARTICLES, METHOD OF SYNTHESIS AND USE AS A NANOVECTOR

(71) Applicant: Luxembourg Institute Of Science And Technology (LIST), Esch/Alzette (LU)

(72) Inventors: Gaelle Corne, Audun-le-Tiche (FR); Damien Lenoble, Wellin (BE); Jean-Sebastien Thomann, Gorcy (FR)

(73) Assignee: LUXEMBOURG INSTITUTE OF SCIENCE & TECHNOLOGY (LIST), Luxembourg (LU)

( * ) Notice: Subject to any disclaimer, the term of this patent is extended or adjusted under 35 U.S.C. 154(b) by 0 days.

(21) Appl. No.: 15/746,357

(22) PCT Filed: Jul. 22, 2016

(86) PCT No.: PCT/EP2016/067546
§ 371 (c)(1),
(2) Date: Jan. 19, 2018

(87) PCT Pub. No.: WO2017/013250
PCT Pub. Date: Jan. 26, 2017

(65) Prior Publication Data
US 2018/0207096 A1    Jul. 26, 2018

(30) Foreign Application Priority Data
Jul. 22, 2015   (LU) .................................... LU92784

(51) Int. Cl.
| | |
|---|---|
| A61K 9/127 | (2006.01) |
| A61K 9/51 | (2006.01) |
| A61K 8/14 | (2006.01) |
| A61K 49/00 | (2006.01) |
| A61Q 19/00 | (2006.01) |

(52) U.S. Cl.
CPC .............. *A61K 9/1271* (2013.01); *A61K 8/14* (2013.01); *A61K 9/127* (2013.01); *A61K 9/1277* (2013.01); *A61K 9/5115* (2013.01); *A61K 49/0002* (2013.01); *A61Q 19/00* (2013.01)

(58) Field of Classification Search
CPC ...... A61K 49/0002; A61K 8/14; A61K 9/127; A61K 9/1271; A61K 9/1277; A61K 9/5115; A61Q 19/00
See application file for complete search history.

(56) References Cited

U.S. PATENT DOCUMENTS

2014/0079774 A1   3/2014  Brinker et al.
2015/0164798 A1*  6/2015  Brinker ................ A61K 9/1277
                                                          424/450

FOREIGN PATENT DOCUMENTS

WO      2014138278 A1    9/2014

OTHER PUBLICATIONS

International Search Report for corresponding PCT/EP2016/067546 dated Oct. 24, 2016.
Selective Functionalization of the Outer and Inner Surfaces in Mesoporous Silica Nanoparticles, Johann Kecht, Axel Schlossbauer, and Thomas Bein, Chem. Mater. 2008, 20, 7207-7214.
Suppression of the Hemolytic Effect of Mesoporous Silica Nanoparticles after Protein Corona Interaction: Independence of the Surface Microchemical Environment, Amauri J. Paula,Diego Stéfani T. Martinez, Roberto T. Araujo Júunior, Antonio G. Souza Filho and Oswaldo L. Alves, J. Braz. Chem. Soc., vol. 23, No. 10, 1807-1814, 2012.
The effect of PEGylation of mesoporous silica nanoparticles on nonspecific binding of serum proteins and cellular responses, Qianjun He, Jiamin Zhang, Jianlin Shi, Ziyan Zhu, Linxia Zhang, Wenbo Bu, Limin Guo, and Yu Chen, Biomaterials 31 (2010) 1085-1092.
Electrostatically Mediated Liposome Fusion and Lipid Exchange with a Nanoparticle-Supported Bilayer for Control of Surface Charge, Drug Containment, and Delivery, Juewen Liu, Xingmao Jiang, Carlee Ashley, and C. Jeffrey Brinker, J. Am. Chem. Soc. 2009, 131, 7567-7569.
Colchicine-Loaded Lipid Bilayer-Coated 50nm Mesoporous Nanoparticles Efficiently Induce Microtubule Depolymerization upon Cell Uptake, Valentina Cauda, Hanna Engelke, Anna Sauer, Delphine Arcizet,Christoph Brauchle, Joachim Radler,Thomas Bein, DOI: 10.1021/nl100991w, Nano Letters 2010, 10, 2484-2492.
Wide Varieties of Cationic Nanoparticles Induce Defects in Supported Lipid Bilayers, Pascale R. Leroueil, Stephanie A. Berry, Kristen Duthie, Gang Han, Vincent M. Rotello, Daniel Q. McNerny, James R. Baker, Jr.,Bradford G. Orr, and Mark M. Banaszak Holl, Nano Letters, 2008 vol. 8, No. 2 420-424.
Cationic Nanoparticles Induce Nanoscale Disruption in Living Cell Plasma Membranes, Jiumei Chen, Jessica A. Hessler, Krishna Putchakayala, Brian K Panama,Damian P. Khan, Seungpyo Hong, Douglas G. Mullen, Stassi C. DiMaggio, Abhigyan Som, Gregory N. Tew, Anatoli N. Lopatin, James R. Baker, Jr., Mark M. Banaszak Holl, and Bradford G. Orr, J. Phys. Chem. B 2009, 113, 11179-11185.

(Continued)

*Primary Examiner* — Michael B. Pallay
(74) *Attorney, Agent, or Firm* — Sandberg Phoenix and Von Gontard

(57) ABSTRACT

A method for manufacturing a negatively charged supported lipid bilayer. The method comprises the steps of preparing a formulation comprising at least three lipids (1,2-dioleoyl-sn-glycero-3-phospho-L-serine (DOPS), cholesterol and at least one lipid different from DOPS and cholesterol) dissolved in a first solvent, of evaporating the first solvent, of adding an aqueous formulation of mesoporous silica nanoparticles, of performing an ultra-sonication and of performing a centrifugation. The method is remarkable in that the number of equivalents of cholesterol relative to one equivalent of DOPS is comprised between 2.30 and 2.70. Additionally, negatively charged supported lipid bilayer on a mesoporous silica nanoparticle comprising cholesterol, 1,2-dioleoyl-sn-glycero-3-phospho-L-serine (DOPS) and at least one lipid different from DOPS and cholesterol.

10 Claims, 12 Drawing Sheets

(56) References Cited

OTHER PUBLICATIONS

Figure 1:
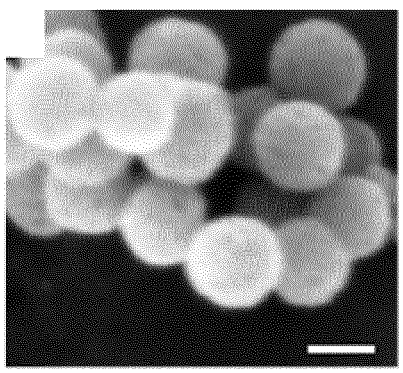

The systemic toxicity of positively charged lipid nanoparticles and the role of Toll-like receptor 4 in immune activation Ranit Kedmi, Noa Ben-Arie, and Dan Peer, Biomaterials 31 (2010) 6867-6875.

A method to evaluate the effect of liposome lipid composition on its interaction with the erythrocyte plasma membrane Joanna Wojewodzka, Grzegorz Pazdzior, and Marek Langner, Chemistry and Physics of Lipids 135 (2005) 181-187.

Mesoporous silica-supported lipid bilayers (protocells) for DNA cargo delivery to the spinal cord, Ellen C. Dengler, Juewen Liu, Audra Kerwin, Sergio Torres, Clara M. Olcott, Brandi N. Bowman, Leisha Armijo, Katherine Gentry, Jenny Wilkerson, James Wallace, Xingmao Jiang, Eric C. Carnes, C. Jeffrey Brinker, and Erin D. Milligan, Journal of Controlled Release 168 (2013) 209-224.

\* cited by examiner

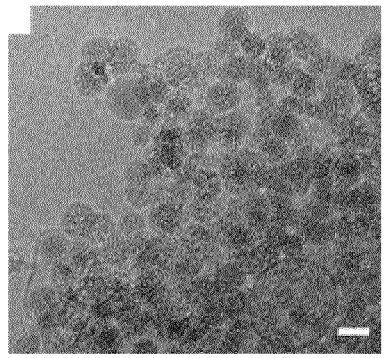
Fig. 20
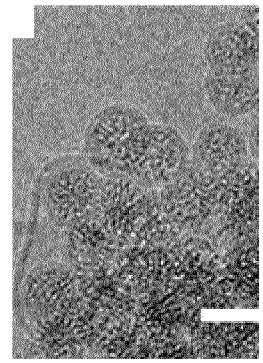
Fig. 21
| Samples | NTA Size in milliQ water (nm) | NTA Size in HEPES Buffer (nm) | NTA Size in Human Serum (nm) |
|---|---|---|---|
| MSNPs | 68 ± 36 | 127 ± 71 | 124 ± 66 |
| MSNPs+ | 99 ± 42 | 187 ± 83 | NA |
| SLB-@MSNPs | 127 ± 43 | 145 ± 69 | 139 ± 72 |
| SLB-iPEG@MSNPs | 149 ± 56 | 149 ± 59 | 134 ± 70 |
Fig. 22

NEGATIVELY CHARGED SELF-ASSEMBLING SUPPORTED LIPID BILAYER ON MESOPOROUS SILICA NANOPARTICLES, METHOD OF SYNTHESIS AND USE AS A NANOVECTOR

CROSS-REFERENCE TO RELATED APPLICATIONS

The present invention is the US national stage under 35 U.S.C. § 371 of International Application No. PCT/EP2016/067546, which was filed on Jul. 22, 2016, and which claims the priority of application LU 92784 filed on Jul. 22, 2015, the content of which (text, drawings and claims) are incorporated here by reference in its entirety.

FIELD

The invention is directed to the field of synthesis of mesoporous silica nanomaterials adapted to be used as nanovector for the encapsulation and the delivery of materials. More particularly, the invention is directed to the synthesis of mesoporous silica nanomaterials which are completely surrounded by a supported lipid bilayer (SLB).

BACKGROUND

Mesoporous silica nanomaterials allow different biomedical applications such as drug delivery, therapeutic imaging, and diagnosis. In this context, mesoporous silica nanoparticles (MSNPs) have been hugely studied as a vector for drug delivery applications.

Mesoporous silica micro or nanoparticles are generally synthesized using template-assisted sol-gel methods.

In order to attach different structure around those MSNPs, such as, for example, a supported lipid bilayer (SLB), it is interesting to be able to functionalize the MSNPs with a reactive moiety which is on the external surface of the MSNPs, allowing subsequently further functionalization.

Among different methods, Bein and co-workers (*Chem. Mater.*, 2008, 20, 7207-7214) have reported the self-assembly of MSNPs, in particular functionalized MSNPs. The self-assembly is provided by mixing a surfactant, which is employed as structure-directing agent, a silica precursor, and an organotriethoxysilane, which will provide the functional moiety onto the external surface of the nanoparticles, in an alkaline aqueous media containing a polyalcohol, which is going to slow down the condensation rate of the silica species.

The surfactant is cetyltrimethylammonium chloride (CTACl).

The silica precursor is tetraethylorthosilicate (TEOS).

The organotriethoxysilane is 3-aminopropyltriethoxysilane (APTES). It can also be, for example, phenyltriethoxysilane (PTES).

The polyalcohol is triethanolamine (TEA).

The protocol provided by the Bein's research group requires the co-condensation of all of the above mentioned reagents to provide the self-assembly of the functionalized MSNPs.

Thus, a first mixture of TEOS, CTACl, TEA in water is prepared and is co-condensed with a mixture of TEOS and the organotriethoxysilane. The second mixture, comprising TEOS and the organotriethoxysilane, always contained 185 µmol of silane, namely 2% of the total amount of silane involved in the preparation of the MSNPs.

The second mixture can be added onto the first mixture at different time, depending of the nanoparticle growth.

By using this above co-condensation principle and such ratio, non-aggregated functionalized MSNPs were obtained. However, the yield of functionalized, namely the yield of organotriethoxysilane incorporated within the external surface of the nanoparticles is dependent of the starting concentration of organotriethoxysilane, which is always below 2% of the total amount of silane involved in the preparation of the MSNPs.

The yield of the functionalization of the nanoparticles with the amino group (using subsequently APTES as organotriethoxysilane) was reported using ζ-potential measurements.

ζ-potential experiments performed after 10 or 30 minutes of particle growth at a pH of 6 indicates a ζ-potential between 0 mV and 5 mV. At more acidic pH values, the ζ-potential logically increases (up to 10 mV at a pH of 4 and up to more than 25 mV at a pH of 2 after 30 minutes of particle growth).

When the co-condensation route was not performed, namely when the organotriethoxysilane (at a concentration equal to 2% of the total amount of silane involved in the preparation of the MSNPs) was added directly (without condensation with TEOS), the final nanoparticles obtained where either aggregated (in the case where APTES was used) or non-functionalized (in the case where PTES was used).

Those results suggest that when the organotriethoxysilane is used at this concentration, the pores and the channels of the nanoparticles in formation becomes blocked. However, when co-condensation is previously performed, the organotriethoxysilanes are hydrolysed forming oligosilicate anions which can subsequently reacts with the silica wall which is built during the nanoparticle growth.

MSNPs are not yet approved for medical application as drug delivery vectors. Divergent results have been discussed and it has been demonstrated that the toxicity and the biodistribution were dependent on the shape, the structure, the functionalization and the size of the silica NP types.

Generally, MSNPs are expected to be administered intravenously and the future capability as carriers will depend on their drug delivery performances and biocompatibility. In this context, several reports have focused on MSNPs hemotoxicity which also depends on the surface functionalization, size and shape. In the literature, most of the hemolysis assays are performed in PBS (phosphate-buffered saline) solution. For instance, Paula and co-workers (*J. Braz. Chem. Soc.*, 2012, 23, 1807-1814) have demonstrated that the protein corona on 40-80 nm MSNPs induced the hemolysis suppression. However, the absence of hemolysis does not mean that there is no impact on red blood cells (RBCs). Reshaping or stress peak formation can hamper the RBCs deformability and therefore the biocompatibility of the system.

Several functionalizations have been tested in order to decrease hemolysis of RBCs induced by MSNPs. A pegylated coating was described by He Q. et al. (*Biomaterials*, 2010, 31, 1085-1092) as very efficient for this purpose. Nevertheless, for drug delivery design, based on PEG coating, let predict a large "burst effect" for hydrophilic drugs and a lesser extent for hydrophobic ones. To circumvent this drawback, the pores can be sealed by using small nanoparticles, polymeric cushions, organic corks or lipids.

In this context, coatings based on supported lipid bilayer (SLB) are emerging and presenting an important advantage in controlling the drug release as well as improving the biocompatibility of MSNPs.

Despite this interest, few methods have been described to achieve the adsorption of a SLB on sub 100 nm MSNPs. Brinker's group synthesized to so-called "protocells" by merging mesoporous MCM-41 nanoparticles with performed and purified liposomes. In their case, nanoparticles sizes were generally greater than 100 nm and the porous matrix was organized like a honeycomb structure. The method of Brinkers and co-workers (*J. Am. Chem. Soc.*, 2009, 131, 7567-7569) involves the synthesis of anionic liposomes, extrusion and mechanical stirring with cationic silica nanoparticles followed by the post insertion of cationic lipids. Without this post insertion, it was suggested that the negatively charged SLB only partially covered the mesoporous core. Bein's group proposed a new method to form SLB on MSNPs of 55 nm based on solvent exchange methods (*Nano Lett.*, 2010, 10, 2484-2492). In their work, however, the fluorescence cross-correlattion (FCCS) method cannot demonstrate directly that the SLB is a non-defect supported bilayer.

This kind of supported bilayer presenting defects suffers from different kind of problems during delivery of materials (e.g. drugs).

Cationic NPs such as cationic silica NPs, cationic gold NPs or polyethylenimine polymer based NPs were demonstrated in several reports as producing defects in plasma membrane models (*Nano Lett.*, 2008, 8, 420-424 and *J. Phys. Chem.*, 2009, 113, 11179-11185).

Cationic lipids NPs which include 1,2-dioleoyl-3-trimethylammonium-propane (DOTAP) lipids were described as potentially toxic, inducing immune toxicity (*Biomaterials*, 2010, 31, 6867-6875) and RBCs lysis (*Chem. Phys. Lipids*, 2005, 135, 181-187).

For non-gene delivery applications, there is no need to use cationic NPs. Consequently, neutral or anionic SLBs can be used. Anionic SLBs may decrease the interaction between RBCs or plasma proteins and therefore increase the stability of MSNPs in blood. However, no method was described to achieve anionic SLB without defect on MSNPs.

International patent application published WO 2014/138278 A1 describes a method for forming a phospholipid bilayer including contacting a suspension of silica bodies, for example, pre-loaded silica bodies, with a solution of phospholipids in a suitable solvent. In this document, the combined mixture can be supplied with energy, for example, via sonication, to facilitate coating of the silica body surface with the phospholipid bilayer. Numerous phospholipids suitable for forming the bilayers are known, including 1,2-dioleoyl-3-trimethylammonium-propane (DOTAP), 1,2-dioleoyl-sn-glycero-3-phospho-L-serine (DOPS) and 1,2-dioleoyl-sn-glycero-3-phosphocholine (DOPC).

In the above described method, it is not required to pre-form phospholipid liposomes that are contacted with the silica bodies. It is rather a preformed film of phospholipids that is contacted with the silica bodies, in order to avoid the need to carry out a lipid phase exchange, which can complicate the process of forming the submicron structures.

SUMMARY

The invention has for technical problem to provide a synthesis of non-aggregated functionalized MSNPs being covered by an anionic SLB without any defect in its structure. The main objective is to enhance the encapsulation of an object, such as for example a drug, within the mesoporous nanoparticles. The goal is also to obtain such SLB which are relatively stable.

The invention is directed to a method for manufacturing a negatively charged supported lipid bilayer on a mesoporous silica nanoparticle, the method comprising the following steps: preparing a formulation of lipids, the lipids being 1,2-dioleoyl-sn-glycero-3-phospho-L-serine alias DOPS, cholesterol and at least one lipid different from DOPS and cholesterol, the formulation of lipids being dissolved in a first solvent; evaporating the first solvent; adding an aqueous formulation of mesoporous silica nanoparticles; performing an ultra-sonication and performing a centrifugation. The method is remarkable in that the number of equivalents of cholesterol relative to one equivalent of DOPS is comprised between 2.30 and 2.70.

According to various embodiments, the number of equivalents of cholesterol relative to one equivalent of DOPS is comprised between 2.35 and 2.65, in various instances between 2.40 and 2.60, for example between 2.45 and 2.55.

In various embodiments, the number of equivalents of cholesterol relative to one equivalent of DOPS is 2.50.

In various embodiments, the step of performing an ultra-sonication is performed at room temperature, under argon and during twenty minutes.

In various embodiments, the at least one lipid different from DOPS and cholesterol is 1,2-dipalmitoyl-sn-glycero-3-phosphocholine alias DPPC.

In various embodiments, the number of equivalents of the DPPC relative to the DOPS is comprised between 3.55 and 3.95, in various instances between 3.60 and 3.90, for example between 3.65 and 3.85, e.g., between 3.70 and 3.80.

In various embodiments, the number of equivalents of the DPPC relative to the DOPS is 3.75.

In various embodiments, the formulation further comprises 1,2-distearoyl-sn-glycero-3-phosphoethanolamine-N-amino(polyethylene glycol) 2 KDa alias DSPE-PEG(2000).

In various embodiments, the number of equivalents of the DPPC relative to the DSPE-PEG(2000) is comprised between 6.70 and 8.30, in various instances between 6.90 and 8.10, for example between 7.10 and 7.90, e.g., between 7.30 and 7.70.

In various embodiments, the number of equivalents of the DPPC relative to the DSPE-PEG(2000) is 7.50.

In various embodiments, the formulation comprising at least three lipids dissolved in a first solvent is prepared at a volume comprised between 0.5 and 1.5 ml, in various instances between 0.75 and 1.25 ml, for example at a volume of 1.0 ml.

In various embodiments, the first solvent is a mixture of chloroform and methanol.

In various embodiments, the number of equivalents of chloroform relative to methanol is comprised between 7 and 11, in various instances between 7.5 and 10.5, for example between 8 and 10, e.g., between 8.5 and 9.5.

In various embodiments, the number of equivalents of the chloroform relative to methanol is 9.0.

In various embodiments, the concentration of lipids in the first solvent is comprised between 2 and 12 mg/ml.

In various embodiments, the mesoporous silica nanoparticles are obtained from the steps of condensing a silica precursor, a surfactant and a condensation agent in a second solvent; of adding an organotriethoxysilane wherein the portion of the organotriethoxysilane to the silica precursor is comprised between 5% and 15%; of removing the surfactant.

In various embodiments, the portion is comprised between 6% and 14%, in various instances between 7% and 13%, for example between 8% and 12%, e.g., between 9% and 11%.

In various embodiments, the portion is 10%.

In various embodiments, the silica precursor is tetraethyl orthosilicate, the surfactant is cetyltrimethylammonium chloride, the condensation agent is triethanolamine and/or the organotriethoxysilane is (3-aminoproplyl)triethoxysilane.

In various embodiments, the number of equivalents of the condensation agent relative to one equivalent of the silica precursor is comprised between 1.6 and 2.4, in various instances between 1.7 and 2.3, for example between 1.8 and 2.2, e.g., between 1.9 and 2.1.

In various embodiments, the number of equivalents of the condensation agent relative to one equivalent of the silica precursor is 2.0.

In various embodiments, the number of equivalents of the surfactant relative to one equivalent of the silica precursor is comprised between 0.22 and 0.30, in various instances between 0.23 and 0.29, for example between 0.24 and 0.28, e.g., between 0.25 and 0.27.

In various embodiments, the number of equivalents of the surfactant relative to one equivalent of the silica precursor is 0.26.

In various embodiments, the organotriethoxysilane is added between 10 minutes and 30 minutes, in various instances between 15 minutes and 25 minutes, for example at 20 minutes.

In various embodiments, the step of removing the surfactant is a combination of a dialysis process and an extraction in hydrochloric acid.

In various embodiments, the second solvent is a mixture of milliQ water and ethanol.

In various embodiments, the number of equivalents of milliQ water relative to one equivalent of the silica precursor is comprised between 100 and 134 or between 217 and 251, in various instances between 105 and 129 or between 222 and 246, for example between 110 and 124 or between 227 and 241, e.g., between 116 and 118 or between 233 and 235.

In various embodiments, the number of equivalents of milliQ water relative to one equivalent of the silica precursor is 117.35 or 234.7.

In various embodiments, the number of equivalents of ethanol relative to one equivalent of the silica precursor is comprised between 2 and 8 or between 9 and 14, in various instances between 3 and 7 or between 10 and 13, for example between 4 and 6 or between 11 and 12.

In various embodiments, the number of equivalents of ethanol relative to one equivalent of the silica precursor is 5.88 or 11.76.

In various embodiments, the mesoporous silica nanoparticles are dissolved in milliQ water at a concentration comprised between 3 and 7 mg/ml, in various instances between 3.5 and 6.5 mg/ml, for example between 4.0 and 6.0 mg/ml, e.g., between 4.5 and 5.5 mg/ml.

In various embodiments, the mesoporous silica nanoparticles are dissolved in milliQ water at a concentration of 5.0 mg/ml.

In various embodiments, the aqueous formulation of mesoporous silica nanoparticle is added at a volume comprised between 3.5 and 4.5 ml, in various instances comprised between 3.75 and 4.25 ml, for example at a volume of 4.0 ml.

The invention is further directed to a negatively charged supported lipid bilayer on mesoporous silica nanoparticle. The negatively charged supported lipid bilayer comprises cholesterol, 1,2-dioleoyl-sn-glycero-3-phospho-L-serine alias DOPS, and at least one lipid different from DOPS and cholesterol. The negatively charged supported lipid bilayer is remarkable in that the number of equivalents of cholesterol relative to one equivalent of DOPS is comprised between 2.30 and 2.70.

In various embodiments, the number of equivalents of cholesterol relative to one equivalent of DOPS is comprised between 2.35 and 2.65, in various instances between 2.40 and 2.60, for example between 2.45 and 2.55.

In various embodiments, the number of equivalents of cholesterol relative to one equivalent of DOPS is 2.50.

In various embodiments, the at least one lipid different from DOPS and cholesterol is 1,2-dipalmitoyl-sn-glycero-3-phosphocholine alias DPPC.

In various embodiments, the number of equivalents of the DPPC relative to one equivalent of the DOPS is comprised between 3.55 and 3.95, in various instances between 3.60 and 3.90, for example between 3.65 and 3.85, e.g., between 3.70 and 3.80.

In various embodiments, the number of equivalents of the DPPC relative to one equivalent of the DOPS is 3.75.

In various embodiments, the negatively charged supported lipid bilayer further comprises 1,2-distearoyl-sn-glycero-3-phosphoethanolamine-N-amino(polyethylene glycol) 2 KDa alias DSPE-PEG(2000).

In various embodiments, the number of equivalents of the DPPC relative to one equivalent of the DSPE-PEG(2000) is comprised between 6.70 and 8.30, in various instances between 6.90 and 8.10, for example between 7.10 and 7.90, e.g., between 7.30 and 7.70.

In various embodiments, the number of equivalents of the DPPC relative to one equivalent of the DSPE-PEG(2000) is 7.50.

In various embodiments, the mesoporous silica nanoparticle comprises at least one silica precursor and at least one organotriethoxysilane, the portion of the organotriethoxysilane to the silica precursor being comprised between 5% and 15%.

In various embodiments, the portion is comprised between 6% and 14%, in various instances between 7% and 13%, for example between 8% and 12%, e.g., between 9% and 11%.

In various embodiments, the portion is 10%.

In various embodiments, the silica precursor is tetraethyl orthosilicate and/or the organotriethoxysilane is (3-aminopropyl)triethoxysilane.

The invention is further directed to a composition adapted for drug delivery which comprises the negatively charged supported lipid bilayer on a mesoporous silica nanoparticle according the teachings of the present invention and at least one active moiety. The composition adapted for drug delivery is remarkable in that the at least one active moiety is a molecule presenting therapeutic properties, in various instances a molecule presenting anticancerous properties, or the at least one active moiety is a contrasting agent, or the at least one active moiety is a cosmetic agent.

In various embodiments, the molecule presenting anticancerous properties is chosen among the following list: doxorubicin, paclitaxel, docetaxel, any mitotic inhibitor, cisplatin, 5-FU, temozolomide, or any other.

In various embodiments, the contrasting agent is any gadolinium derivative, any iodine derivative, any gold derivative, indocyanine green, rhodamine, fluorescein, methylene blue, 5-aminolevulinic acid, any porphyrin precursor, or any other.

In various embodiments, the cosmetic agent is retinoic acid, vitamin E, nicotinic acid, ascorbic acid, any B vitamin, any antioxidant, or any other.

The invention is particularly interesting in that it discloses a method for manufacturing negatively charged supported lipid bilayer on a mesoporous silica nanoparticle, the supported lipid bilayer fully covering the nanoparticle. In addition to the complete covering of the nanoparticle, the method also provide negatively charged supported lipid bilayer with an important colloidal stability. Encapsulation of objects, such as for example a drug, and delivery of these objects to a selective location is therefore considerably enhanced by using this kind of nanoparticles fully covered by those stable supported lipid bilayer.

DRAWINGS

FIG. 1 exemplarily illustrates a SEM (Scanning Electron Microscope) picture of MSNPs, with a size of 53±6 nm (50 counts, scale bar=50 nm).

Figure 2:
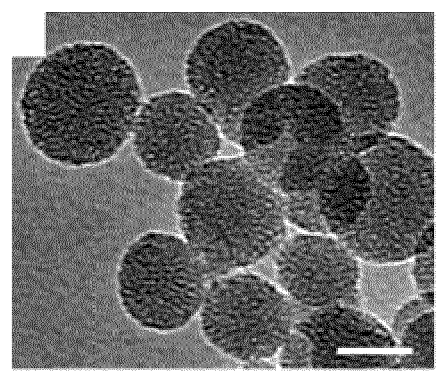

FIG. 2 exemplarily illustrates a TEM (Transmission Electron Microscope) picture of MSNPs, with a size of 53±6 nm (scale bar=50 nm).

Figure 3:
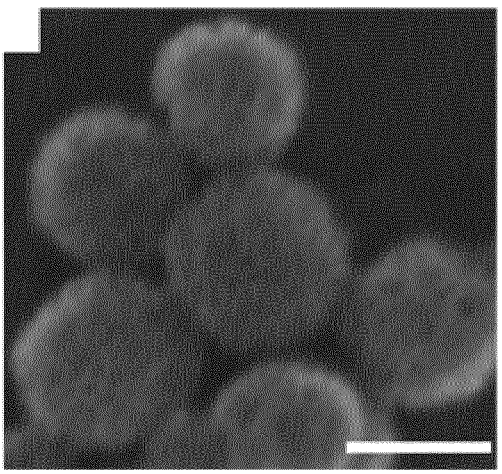

FIG. 3 exemplarily illustrates SEM picture of MSNPs, with a size of 35±6 nm (50 counts, scale bar=35 nm).

Figure 4:
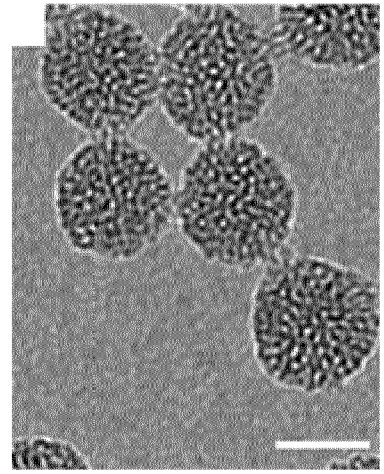

FIG. 4 exemplarily illustrates a TEM picture of MSNPs, with a size of 35±6 nm (scale bar=35 nm).

Figure 5:
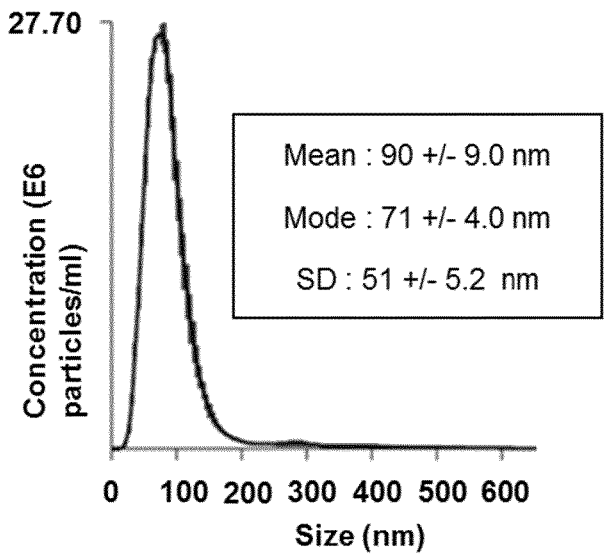

FIG. 5 exemplarily illustrates NTA (Nano Tracking Analysis) of MSNPs, with a size of 35±6 nm.

Figure 6:
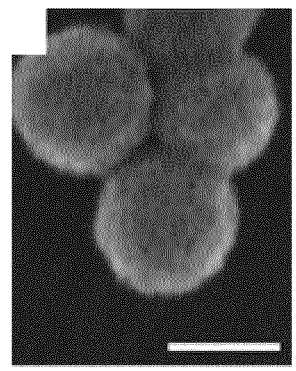

FIG. 6 exemplarily illustrates a SEM picture of MSNPs+, with a size of 50.9±3.6 nm (50 counts, scale bar=50 nm).

Figure 7:
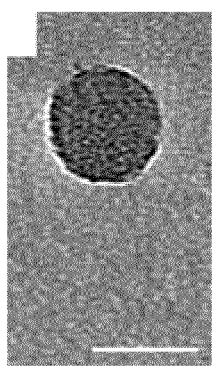

FIG. 7 exemplarily illustrates a TEM picture of MSNPs+, with a size of 50.9±3.6 nm (scale bar=50 nm).

Figure 8:
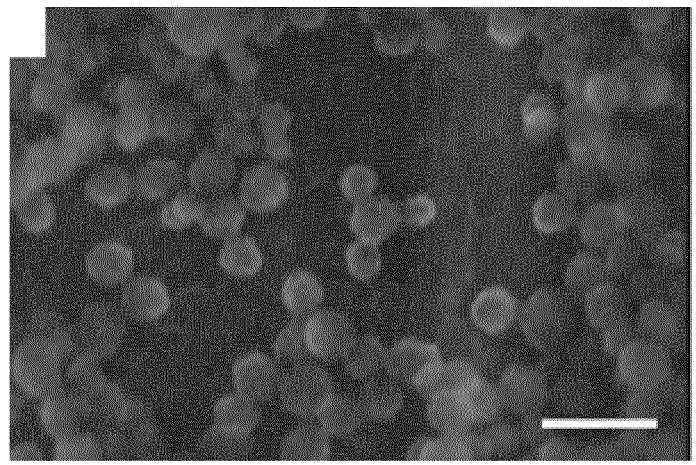

FIG. 8 exemplarily illustrates a SEM picture of MSNPs+, with a sized of 36.5±5 nm (50 counts, scale bar=100 nm).

Figure 9:
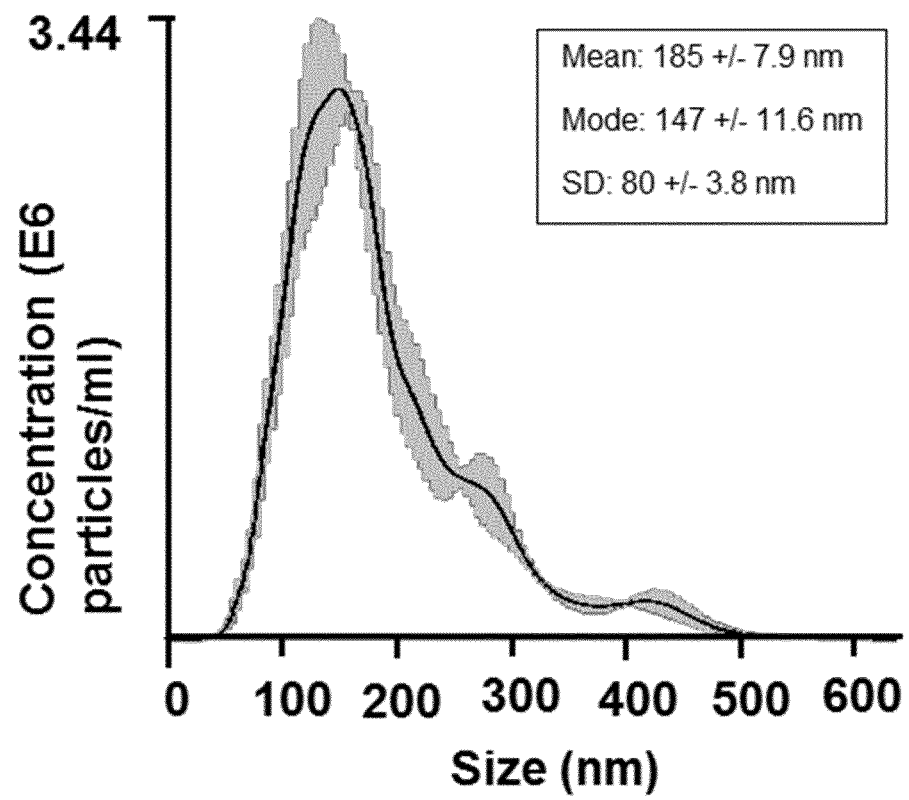

FIG. 9 exemplarily illustrates NTA analysis of MSNPs+, with a sized of 36.5±5 nm.

Figure 10:
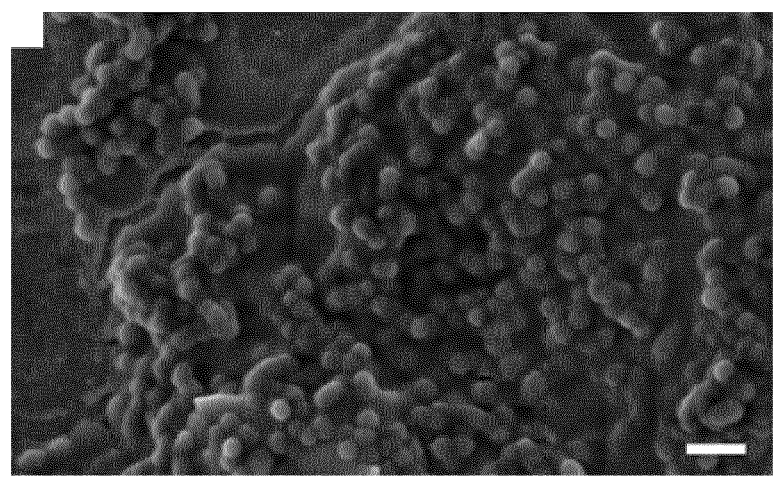

FIG. 10 exemplarily illustrates a SEM picture of purification in ammonium nitrate extraction of MSNPs showing the presence of CTACl template and the aggregation between the nanoparticles (scale bar=200 nm).

Figure 11:
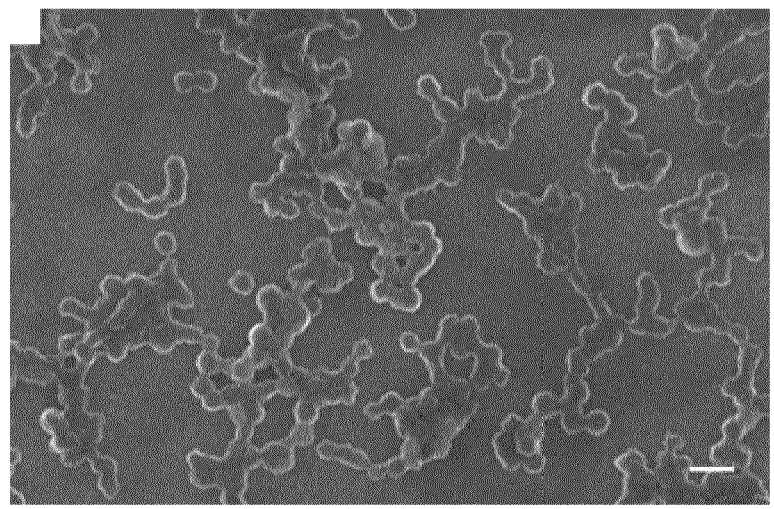

FIG. 11 exemplarily illustrates a SEM picture of MSNPs after the acid dialysis process (scale bar=200 nm).

Figure 12:
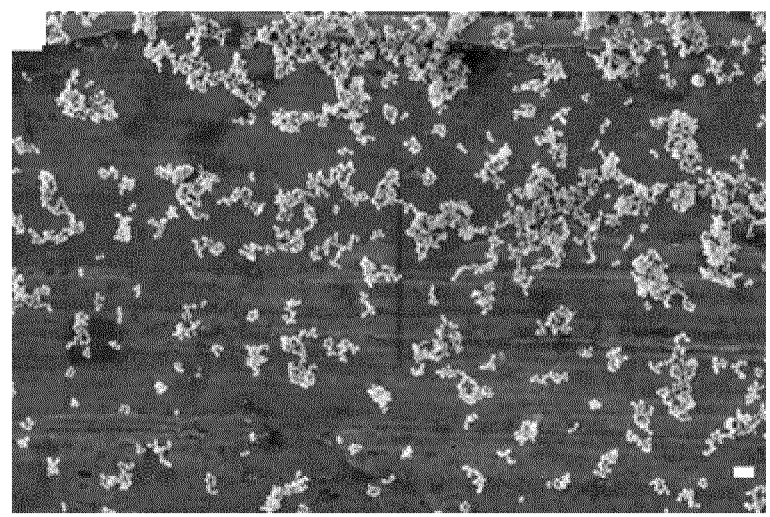

FIG. 12 exemplarily illustrates a SEM picture of the MSNPs dispersed in water after total extraction (scale bar=200 nm).

Figure 13:
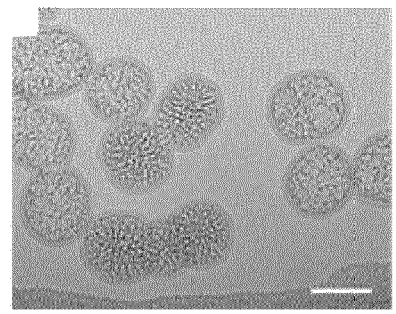

FIG. 13 exemplarily illustrates a CRYO-TEM picture of MSNPs covered by SLB, with a size of 62.3±6.5 nm and a SLB size of around 4.7±0.6 nm.

Figure 14:
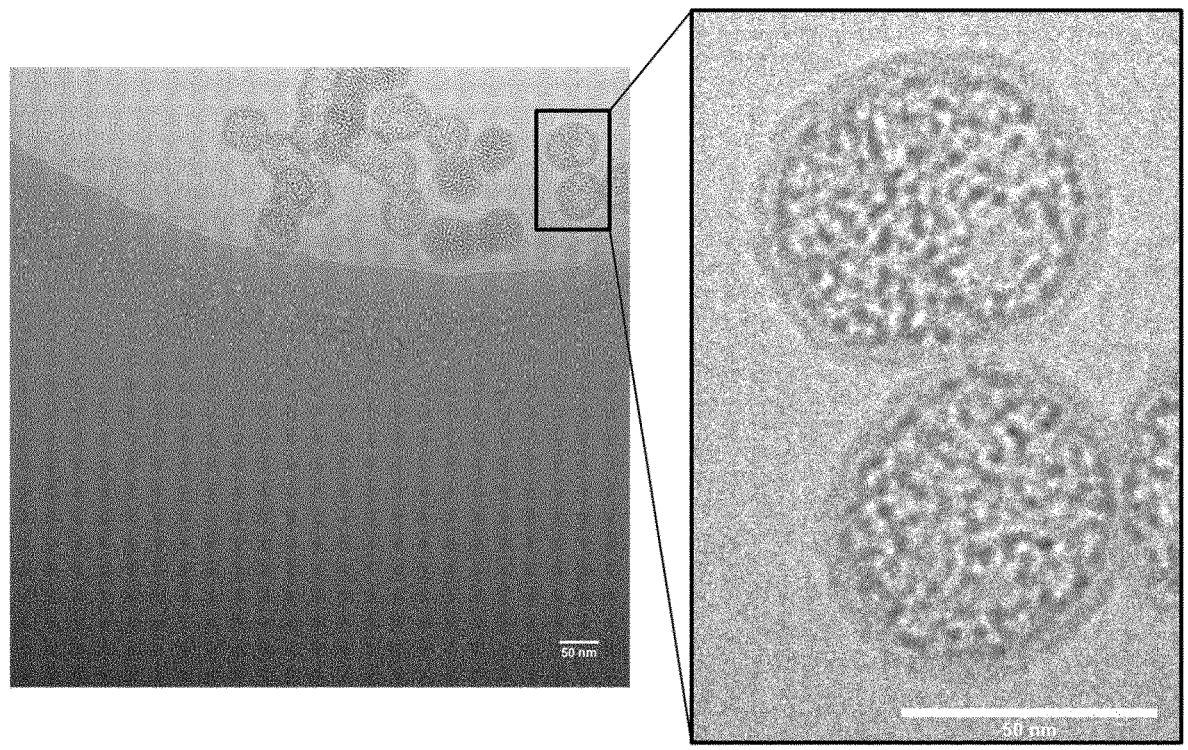

FIG. 14 exemplarily illustrates a CRYO-TEM picture of MSNPs covered by SLB showing the integrity of the SLB.

Figure 15:
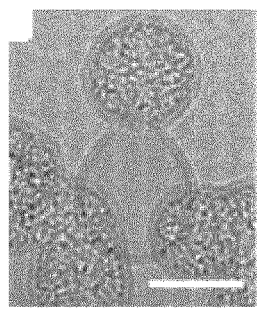

FIG. 15 exemplarily illustrates a CRYO-TEM picture of MSNPs covered by SLB, showing the emergence of a liposome around the MSNPs.

Figure 16:
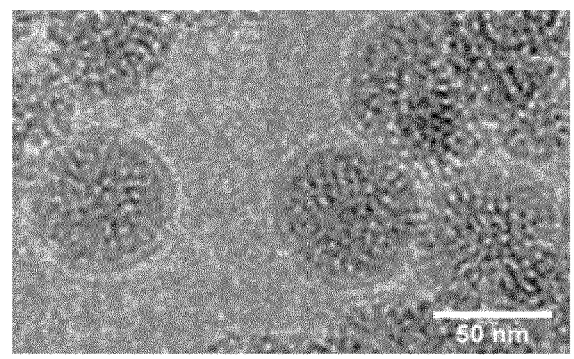

FIG. 16 exemplarily illustrates a CRYO-TEM picture of MSNPs covered by $SLB^{PEG}$, with a size of 65.3±1.6 nm.

Figure 17:
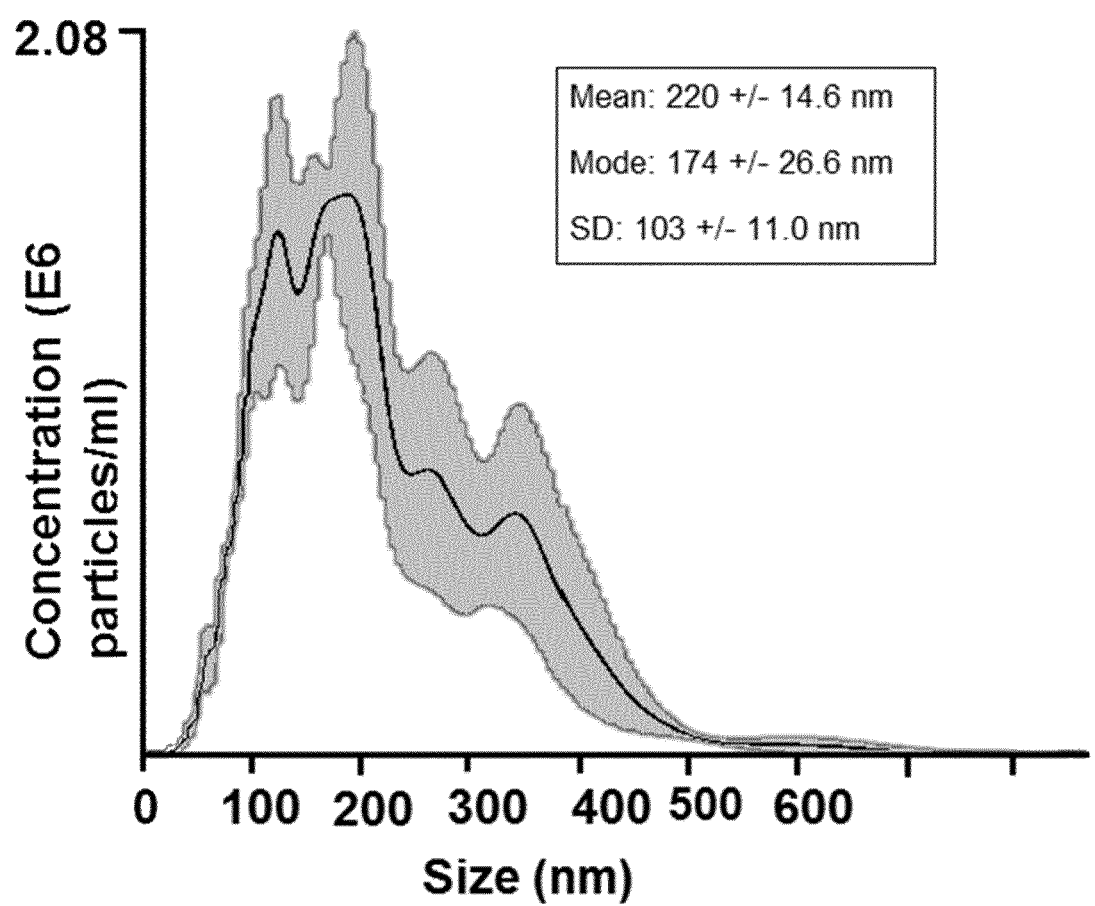

FIG. 17 exemplarily illustrates NTA (Nano Tracking Analysis) of synthesis performed according to prior art protocol.

Figure 18:
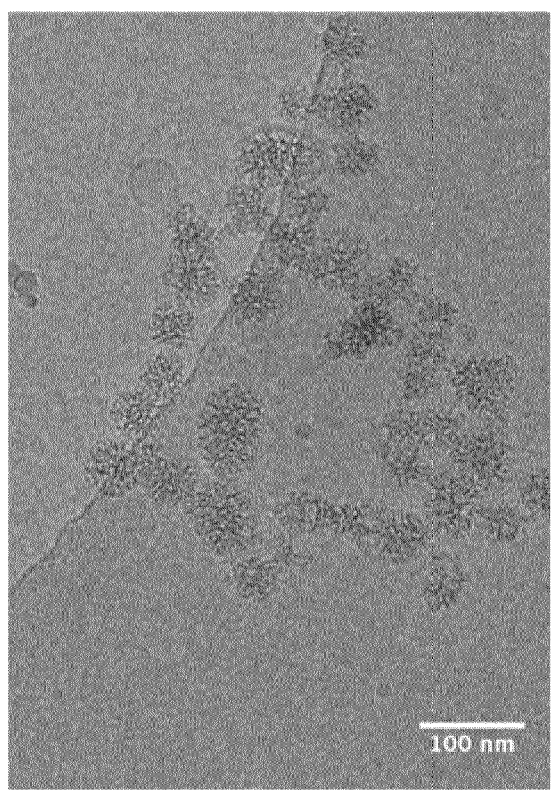

FIG. 18 exemplarily illustrates a CRYO-TEM picture of synthesis performed according to prior art protocol.

Figure 19:
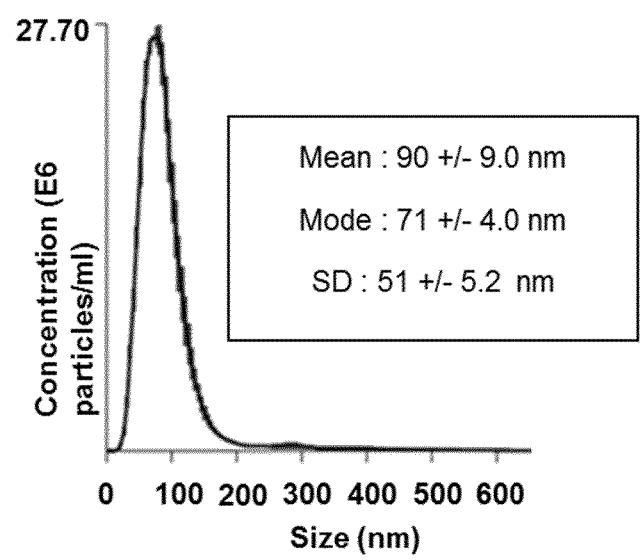

FIG. 19 exemplarily illustrates NTA analysis of MSNPs, with a size of 35±6 nm.

FIG. 20 exemplarily illustrates CRYO-TEM pictures of MSNPs covered by SLB, with a size of the MSNPs of 35±6 nm.

FIG. 21 exemplarily illustrates CRYO-TEM pictures of MSNPs covered by SLB (zoom area on the MSNPs inside one liposome), with a size of the MSNPs of 35±6 nm.

FIG. 22 exemplarily illustrates a size analysis of silica nanoparticles by Nano Tracking Analysis (NTA).

Figure 23:
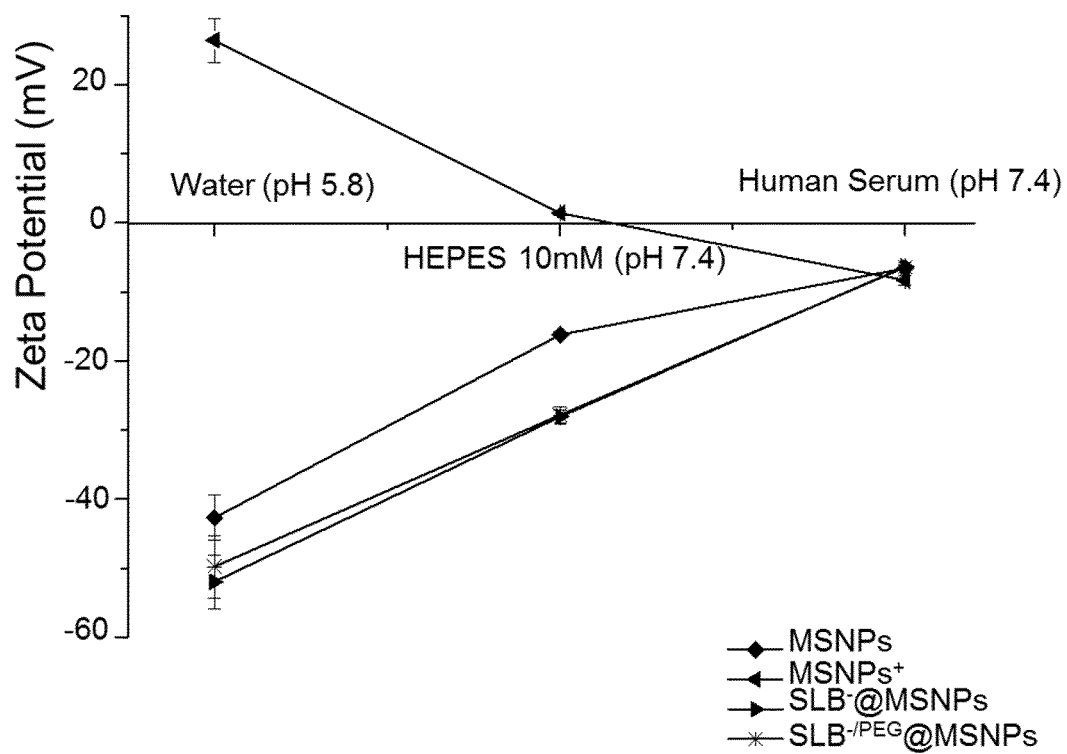

FIG. 23 exemplarily illustrates a ζ-potential graph for MSNPs, MSNPs+, SLB on MSNPs and $SLB^{PEG}$ on MSNPs performed on a Malvern Instruments. Data are mean±SE and represent three independent experiments.

Figure 24:
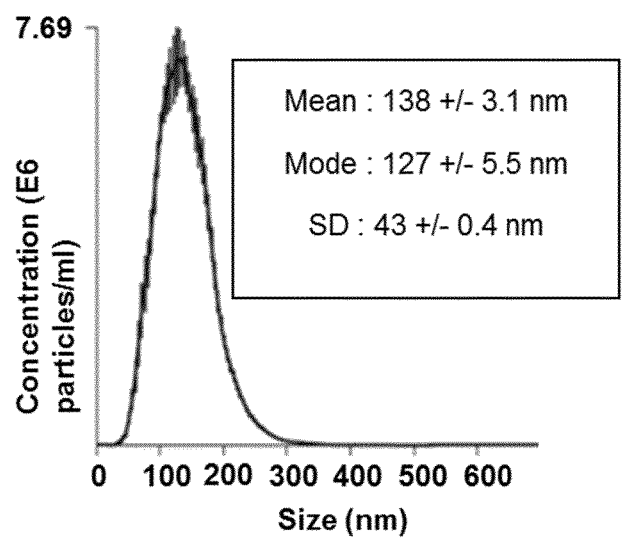

FIG. 24 exemplarily illustrates NTA analysis of SLB on MSNPs in HEPES buffer.

Figure 25:
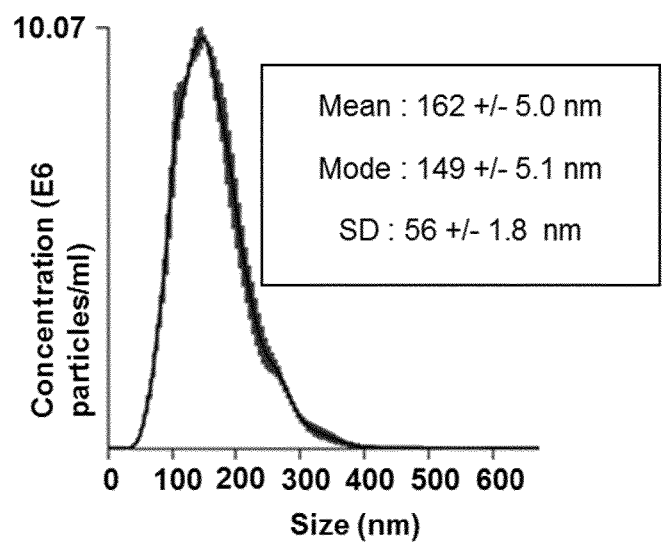

FIG. 25 exemplarily illustrates NTA analysis of $SLB^{PEG}$ on MSNPs in HEPES buffer.

Figure 26:
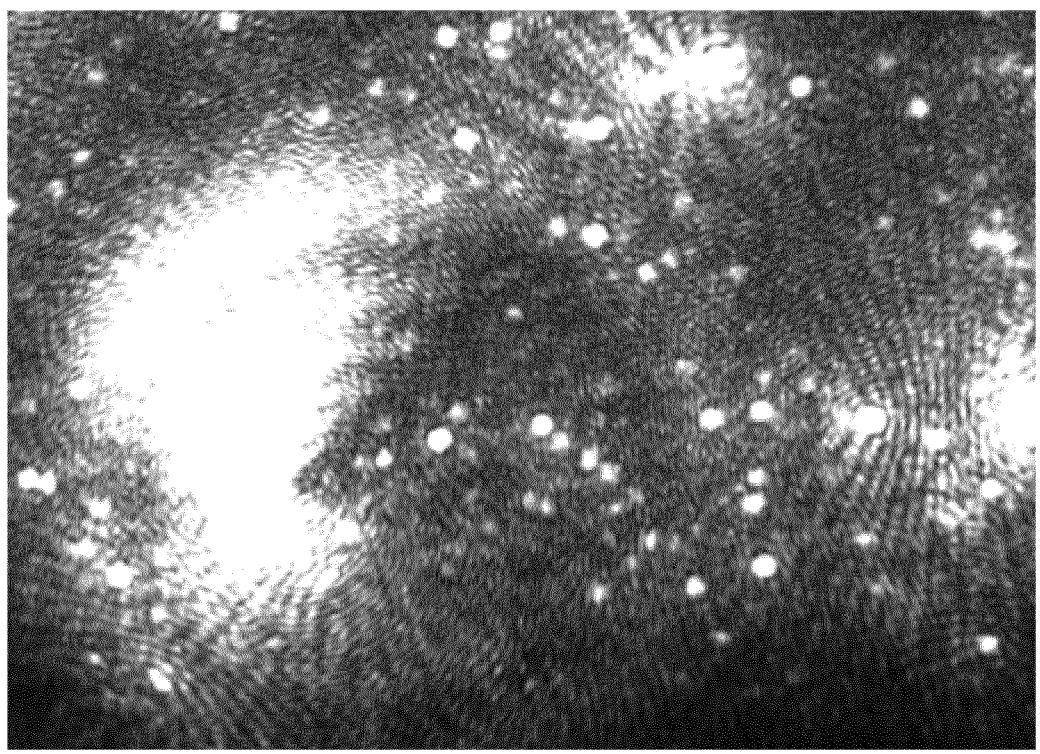

FIG. 26 exemplarily illustrates frames of NTA analysis for MSNPs in human serum.

Figure 27:
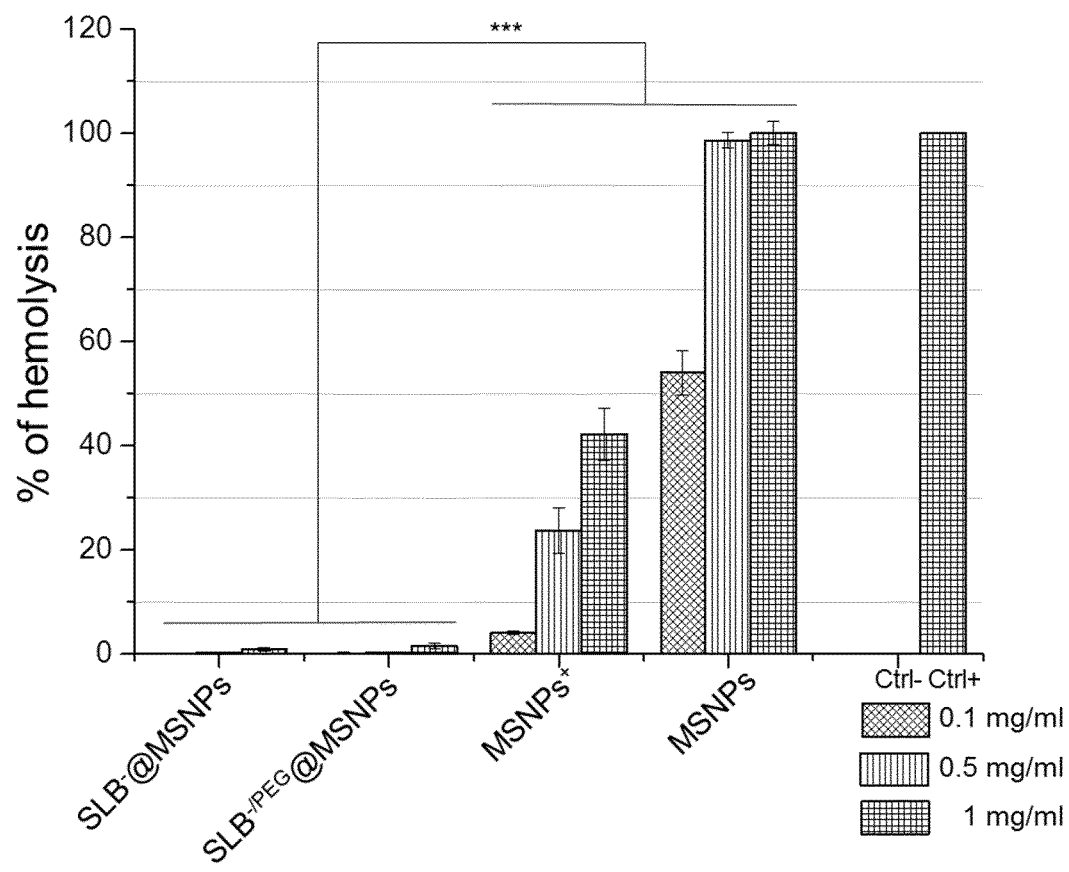

FIG. 27 exemplarily illustrates quantification of released haemoglobin expressed in percentage of hemolysis in PBS buffer. Height of the columns corresponds to the mean values±SE. Ctrl−: negative control (PBS alone) Ctrl+: positive control (milliQ water alone).

Figure 28:
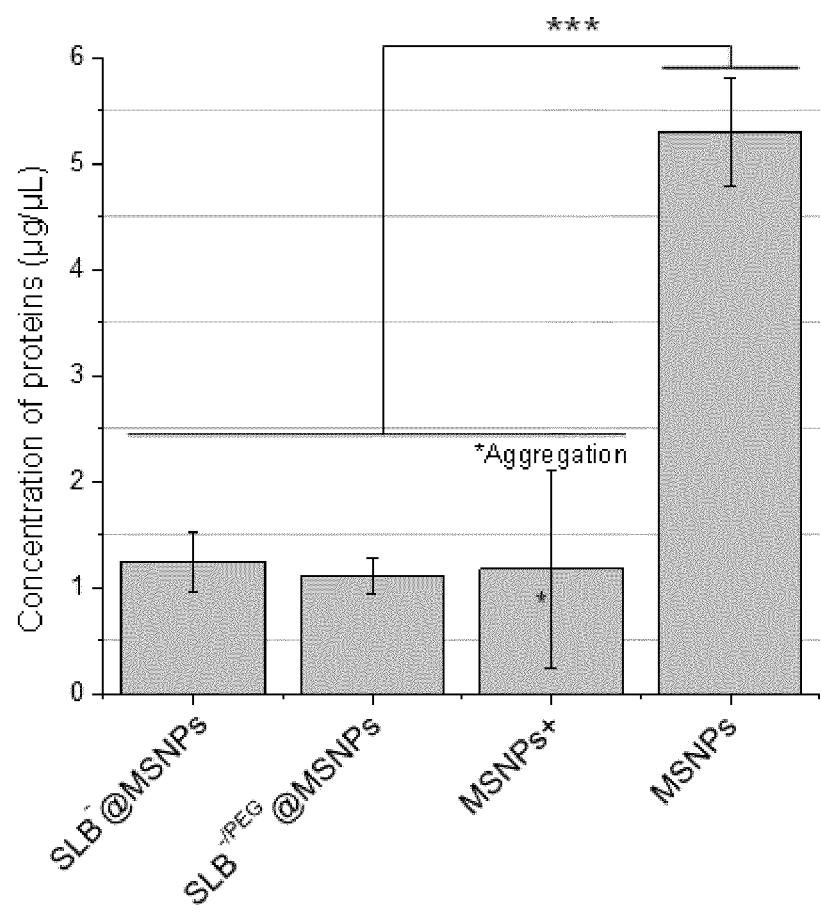

FIG. 28 exemplarily illustrates quantification of adsorbed plasma proteins on the surface of $SLB^-$@MSNPs, $SLB^-_{PEG}$@MSNPs, MSNPs+ and MSNPs. Data are mean±SE. The comparison between columns provides a p<0.001 performed on three independent experiments. NPs were incubated in human plasma for 1 h.

DETAILED DESCRIPTION

The self-assembling of the mesoporous structure was provided by a radial growth using tetraethyl orthosilicate (TEOS) as silica precursor, the surfactant cetyltrimethylammonium chloride solution (CTACl) as a pore template, and triethanolamine (TEA) as condensation agent.

This synthesis formed non-aggregated MSNPs with a dry size of about 54 nm as shown by TEM and SEM pictures (FIGS. 1 and 2).

Smaller MSNPs have potential interest in the perspective to cross biological barriers such as the blood brain barrier. For this purpose, the size of MSNPs was decreased by diluting by two the reagents to get particles of a size around 35 nm. Decreasing concentrations of reactants slows down the condensation of the silica nuclei which can explain the smaller size of these MSNPs (FIGS. 3 and 4).

A minor but still significant intra-particular aggregation of MSNPs 35 nm was observed during hydrodynamic size studies by using Nano Tracking Analysis (NTA) (FIG. 5). Due to their smaller size, MSNPs of 35 nm tend to aggregate more in water than those of 55 nm.

Functionalization of MSNPs with amino moieties provides positively charged nanoparticles. Those positively charged nanoparticles (MSNPs+) will be used to be incorporated into negatively charged structures, such as negatively charged supported lipid bilayer.

A high density of amino moieties is expected to reinforce electrostatic interaction between the negatively charged supported lipid bilayer and the MSNPs+. To achieve such an amino coating, (3-aminopropyl)triethoxysilane (APTES) were added 20 minutes after the beginning of the MSNPs 55 and 35 nm synthesis. Due to the presence of the template CTACl which cloaks the pores, this process allows to functionalize the outer nanoparticle surface prior to the inner surface. However, a functionalization of the inner surface cannot be excluded due to the diffusion of APTES inside the nanoparticle.

FIGS. 6 and 7 provide respectively a SEM and a TEM picture of the MSNPs+ with a size of 50.9±3.6 nm.

A minor increase of size is observed compared to non-functionalized MSNPs. A similar amino coating process was developed for MSNPs of 35 nm. SEM characterization of MSNPs+ (35 nm) is shown in FIG. 8. The dry size of these particles does not significantly changes compared to the non-functionalized MSNPs of 35 nm. Nevertheless, in water, MSNPs+ (35 nm) tends to aggregate more than MSNPs (35 nm) as shown by the NTA analysis depicted in FIG. 9.

In order to remove the template inside MSNPs+ and MSNPs, several extraction methods were tested. Template extraction based on acidic conditions and ionic competition was described to decrease particle aggregation compared to the template calcination. Some methods based either on ethanol/HCl extraction, acid dialysis or ammonium nitrate extraction were already published.

Nevertheless, applying these approaches on our NPs failed to completely remove the template as shown by the SEM analysis (FIGS. 10 and 11).

Successful combination of acid dialysis and extraction in ethanol/HCl was highly efficient as demonstrated on FIG. 12 depicting a SEM picture of the MSNPs dispersed in water after total extraction.

Anionic supported lipid bilayers (SLB) on functionalized MSNPs were synthesized in a one pot process using ultra-sonication. The ultra-sonication process allows indeed the incorporation of the MSNPs+ within the SLB.

The lipid formulations of supported lipid bilayer covering mesoporous silica nanoparticles were composed of 1,2-dioleoyl-sn-glycero-3-phospho-L-serine (DOPS), 1,2-dipalmitoyl-sn-glycero-3-phosphocholine (DPPC), and cholesterol.

In order to obtain a PEG coating, 1,2-distearoyl-sn-glycero-3-phosphoethanolamine-N-amino(polyethylene glycol)-2 KDa (DSPE-PEG (2000)) is further added.

When preparing the formulation, the lipids are dissolved in a solvent, in various instances a mixture of chloroform/methanol at a molar ratio of 9/1.

To form the thin lipid film, 1 ml of the formulation is then evaporated to remove the solvent.

The lipid film constituted by DPPC/DOPS/cholesterol or by DPPC/DOPS/cholesterol/DSPE-PEG(2000) was thus ultra-sonicated in the presence of 4 ml of an aqueous solution of functionalized MSNPs with a nanoparticle size of 50.9±3.6 nm.

The concentration of the aqueous solution of functionalized MSNPs is fixed at 5 mg/mL.

Ultra-sonication of the lipid film in water induces very high shearing forces generating the formation of Small Unilamellar Vesicles (SUV) from MultiLamellar Vesicles (MLV). In the presence of a cationic mesoporous matrix, such as MSNPs+, lipid reorganization might occur in two different ways.

The first mechanism may involve the in situ formation of SUV which will be quickly adsorbed on the mesoporous core according to the mechanism proposed by Brisson and co-workers.

In the second hypothesis, MSNPs can be loaded inside lipid vesicles. Then, the lipid bilayer will merge with the outer layer of the MSNPs due to electrostatic forces and/or hydrogen bonding.

At the end of the process, the stable colloidal suspension was then centrifuged to remove the excess of liposomes and the particles were suspended in water.

To visualize the integrity of the SLB, CRYO-TEM experiments were performed on the suspension of MSNPs covered by SLB (SLB@MSNPs) (FIG. 13). All of the MSNPs+ (51 nm) were perfectly encapsulated by the negative lipid bilayer DPPC/DOPS/cholesterol leading to an average size of 62.3±6.5 nm. The size of the bilayer is about 4.7±0.6 nm.

No defect inside the lipid bilayer was observed from the CRYO-TEM picture, as indicated by FIG. 14.

Interestingly, FIG. 15 shows an "intermediate" particle where one of the MSNPs+ is going to be trapped by anionic liposomes. This picture suggests that the mechanism of interaction is driven by electrostatic forces and could fit in with a two-step mechanism involving the loading of MSNPs+ within a liposome in formation followed by an adsorption of the anionic bilayers on the cationic MSNPs+.

Using ultra-sonication, pegylated SLB have also been synthesized on MSNPs of 65.3±1.6 nm, measured by CRYO-TEM (FIG. 16).

After formulation, lipids were extracted and then quantified using the Liquid Chromatography-Mass Spectrometry (LC-MS) method. Table 1 summarizes the different molar ratios for each lipid before and after the synthesis of the MSNPs incorporated either within the SLB or within the SLB$^{PEG}$.

TABLE I

Initial molar ratios of each lipid before synthesis and final ratios after synthesis and purification of the MSNPs with either SLB or SLB$^{PEG}$. The data are mean ± SE, performed by LC-MS in three independent experiments.

| | | DPPC | DOPS | cholesterol | DSPE-PEG(2000) |
|---|---|---|---|---|---|
| Initial ratio | SLB | 52 | 14 | 34 | N/A |
| | SLB$^{PEG}$ | 48 | 13 | 32 | 7 |
| Ratio after synthesis | SLB | 41.5 ± 2.9 | 8.1 ± 2.3 | 50.3 ± 8.2 | N/A |
| | SLB$^{PEG}$ | 41.9 ± 8.2 | 7.6 ± 1.3 | 36.6 ± 1 | 14 ± 2.1 |

Variations can be seen between the lipids molar ratios before ultra-sonication and the final ratios found by LC-MS after the synthesis. The final molar ratio of cholesterol in the SLB increases from 34% to 50% whereas it remains almost unchanged when the SLB$^{PEG}$ is used. The final molar ratios of DOPS in both formulations are almost divided by two. The final molar ratio of DSPE-PEG 2 KDa is doubled compared to the initial ratio and proves that DSPE-PEG was successfully integrated inside the SLB$^{PEG}$ on MSNPs (SLB$^{PEG}$@MSNPs).

This high amount of cholesterol (36%-50%) in the final SLB is necessary to give colloidal stability to the SLB. This is provided by the number of equivalents (2.50) of cholesterol relative to one equivalent of DOPS as initial molar ratio.

These trends are attributed to the dynamic exchange between the different lipid constituents during the ultra-sonication process. The negatively charged DOPS might have more affinity with ammonium moieties compared to silanol domains, whereas DPPC might be more prone to be adsorbed on silanol functions. Therefore, during ultra-sonication, lipids in excess are able to self-assemble to build the most thermodynamically stable SLB which can explain these variations between the lipid molar ratios before and after the synthesis.

In order to assess if the ultra-sonication process improves the synthesis of SLB on MSNPs, as compared with the methods used by Brinker and co-workers (*J. Control. Release*, 2013, 168, 209-224) which is based on the adsorption of preformed liposomes on the silica surface, SUV liposome DPPC/DOPS/cholesterol (80 nm) was mechanically mixed with MSNPs+ (55 nm) in water. After the removal of the liposomes excess and particle redispersion, sizes were analyzed using Nano Tracking Analysis (NTA), showing aggregation (FIG. 17) and CRYO-TEM, showing no synthesis of SLB at all (FIG. 18). These results demonstrate that the SLB incorporating the MSNPs through an ultra-sonication step according to the present invention provided a greater stability than a simple adsorption of preformed liposomes on the silica surface of the nanoparticles.

When using MSNPs+ with a size of 36.5±5 nm, no stable colloidal suspension of SLB on MSNPs can be obtained. Indeed, a minor but still significant intra-particular aggregation of MSNPs 35 nm was observed during hydrodynamic studies by using Nano Tracking Analysis (NTA) (FIG. 19).

Covering MSNPs 35 mm with SLB results in a strong aggregation of the particles after purification. This may be explained by the initial intra-particular aggregation of MSNPs+ 35 nm and the NPs curvature which is significantly higher than the 55 nm MSNPs. This may induce defects in the SLB and concomitant intra-particulate aggregation between cationic silica domains and SLB negatively charged domains. Nevertheless the presence of intact or partial SLB on MSNPs+ (35 nm) can be seen in the aggregate as shown by CRYO-TEM pictures (FIGS. 20 and 21).

The ζ-potential of SLB or $SLB^{PEG}$ on MSNPs were investigated in different media (milliQ water, HEPES buffer and human serum) and were compared with the similar physicochemical properties of MSNPs and MSNPs+ (FIGS. 22 and 23). These measurements have been made without performing any filtration or size exclusion prior to analysis. The size has been measured using NTA whereas ζ-potential has been measured by using Malvern Nano Zetasizer®. In milliQ water, at a pH value of 5.8, MSNPs+ have a charge of +26.47 mV whereas SLB on MSNPS or $SLB^{PEG}$ on MSNPs have a charge of −52 and −50 mV respectively. This is in agreement with the CRYO-TEM pictures (FIGS. 14 and 16) showing that the MSNPs+ are fully coated by SLB or $SLB^{PEG}$.

In comparison with the results obtained by the Bein's research group, for a similar value of pH, the ζ-potential of the MSNPs+ of the present invention is significatively higher. Indeed, at a pH value of 6.0, the ζ-potential of the Bein's nanoparticle is comprised between 0 mV and 5 mV. This is a clear indication that the functionalization of the MSNPs by the organotriethoxysilane, i.e. (3-aminopropyl) triethoxysilane (APTES), resulting in MSNPs+, namely in nanoparticles bearing a reactive organic group at its external surface, proceeds in a more efficacious manner when the protocol according to present invention is followed.

A further result (not shown) indicates that at a pH value of 4.0, the ζ-potential measurement demonstrates a charge of +37 mV onto the MSNPs+.

The presence of a large number of reactive organic groups at the external surface of the MSNPs+, in particular the presence of a large number of amino group, coupled with the high amount of cholesterol in the final SLB, enhance the incorporation and the stability of those nanoparticles into the SLB. More particularly, the self-assembled mesoporous silica nanoparticle is entirely covered by the SLB.

Therefore, the encapsulation of any types of objects within the self-assembled nanoparticle is considerably enhanced.

The size of MSNPs+ in water is about 99 nm. This may be attributed to the presence of a few intra-particulate aggregates due to $NH_3^+$/Si—OH electrostatic or hydrogen bonding between the particles. SLB on MSNPs were formulated in water from MSNPs+ resulting in the size of 127 nm which is higher than MSNPs+. This can be explained by the lipid coating present on the surface of MSNPs+.

The SLB on MSNPS and $SLB^{PEG}$ on MSNPs are stable in HEPES buffer (pH=7.4) with a monodisperse distribution centered respectively around 127 nm and 149 nm (FIGS. 24 and 25).

When the particles are suspended in human serum (pH=7.4), ζ-potential has a value close to −10 mV whatever the kind of nanoparticle. This can be explained by the masked charges due to the protein corona. However, monodispersion in human serum is kept for MSNPs and SLB on MSNPs suggesting high stability of these particles whereas the size of MSNPs+ cannot be measured by NTA due to the strong aggregation above 1 μm (FIG. 26). Together, these results indicate that SLB on MSNPS and $SLB^{PEG}$ on MSNPs have an excellent colloidal stability in this biologic fluid compared to MSNPs+ (without SLB).

Biological Experiments on MSNPs and on SLB@MSNPs.

Systemic administration of nanotechnology based drug delivery platforms are moderated by the biosafety of these materials. Compared with small molecules e.g. drugs or contrast media their physical nature can induce interactions with cells and blood components. Cationic liposomes and cationic particles were originally designed as gene delivery vectors. However, the toxicity of cationic lipids remains an issue especially for drug delivery applications. In order to use those negatively charged particles for future intravenous drug delivery application, the cytotoxicity of SLB on MSNPs and $SLB^{PEG}$ on MSNPs have been investigated. The toxicity of SLB nanoparticles was compared to MSNPs and MSNPs+. Hemolysis assays can evaluate the influence of nanoparticles on isolated human red blood cells (RBCs) membrane. The disruption of RBCs membrane was quantified by measuring the absorbance of released hemoglobin at 540 nm in supernatants after centrifugation (FIG. 27).

MSNPs in PBS, induce a high rate of hemolysis even at low concentrations up to the equivalence with the water positive control effect (100% of hemolysis) at the high concentrations.

Coating of MSNPs by amino groups curbs their hemolytic effect (p values <0.001) that remains at 20% and 40% for 0.5 and 1 mg/mL respectively. On the contrary, no hemolysis of RBCs was observed with SLB on MNSPs and $SLB^{PEG}$ on MNSPs even at a very high concentration (1 mg/ml). Compared with MSNPs, this interesting absence of hemolytic effect in PBS could be correlated with the lower surface energy of SLB compared to MSNPs and MSNPs+.

EXPERIMENTAL SECTION

Nanoparticles Synthesis.
Chemical Materials.
Cetyltrimethylammonium chloride solution (CTACl), TEA: Triethanolamine, tetraorthosilicate (TEOS), (3-aminopropyl)triethoxysilane (APTES) and cholesterol were purchased from Sigma-Aldrich Co. The phospholipids 1,2-dioleoyl-sn-glycero-3-phospho-L-serine (DOPS), 1,2-dipalmitoyl-sn-glycero-3-phosphocholine (DPPC) and 1,2-distearoyl-sn-glycero-3-phosphoethanolamine-N-[amino (polyethylene glycol)-2000] (DSPE-PEG 2 KDa) were purchased from Avanti Polar Lipids Inc. (Alabaster, Ala.). Ammonium acetate and Methanol were purchased from Biosolve.

Synthesis of 55 nm Mesoporous Silica Nanoparticles (MSNPs 55 mn).

A stock solution was prepared by mixing 13.75 mL (762.8 mmol) of milliQ water, 2.23 mL (38.2 mmol) of absolute ethanol, and 2.23 mL (1.69 mmol) of 25% CTACl by stirring in Radleys Tech® carrousel for 10 minutes under argon atmosphere. Then, TEA (1.78 mL; 13.37 mmol) was added and mixed with stock solution until complete dissolution. Stock solution was heated at 60° C., and then TEOS (1.454 mL; 6.5 mmol) was added in drops over 2-3 minutes. The reaction was stirred for 2 hours, under argon atmosphere. The molar ratio of this reaction is: TEOS/CTACl/TEA/H$_2$O/EtOH 1/0.26/2/117.35/5.88. The mesoporous silica nanoparticles which are formed display a wormhole-type matrix.

Synthesis of 35 nm Mesoporous Silica Nanoparticles (MSNPs 35 nm).

During this reaction, the reagent mixture was diluted by two. Stock solution was prepared by mixing 27.5 mL (1.52 mol) of milliQ water, 4.46 mL (76.4 mmol) of absolute ethanol, and 2.23 mL (1.69 mmol) of 25% CTACl in Radleys Tech® carrousel for 10 minutes under argon atmosphere. Then, the same synthesis process than the MSNPs 55 nm is applied with a molar ratio of: TEOS/CTACl/TEA/H2O/EtOH 1/0.26/2/234.7/11.76. The mesoporous silica nanoparticles which are formed display a wormhole-type matrix.

Synthesis of Mesoporous Silica Nanoparticles positively charged (MSNPs+).

After 20 minutes of MSNPs 55 nm reaction, 150 µL of APTES (0.64 mmol) were added inside the solution. The reaction was stirred for 2 hours, under argon atmosphere. The molar ratio of this reaction is:

TEOS/CTACl/TEA/H2O/EtOH/APTES 1/0.26/2/117.35/5.88/0.1.

Template Extraction.

The template extraction was performed by the combination of dialysis process and washing in hydrochloric acid. For the dialysis process, 50 mL of mesoporous silica nanoparticles were transferred into a dialysis membrane composed of cellulose (Molecular Weigh Cut Off=15 000 Da, Spectrum Labs)). Nanoparticles were washed during 24 h against 1 L of the mixture containing 3M acetic acid, and ethanol (1:1) to remove CTACl from inside nanoparticle pores. This process was repeated five times. To remove the residual surfactant, the NPs were washed in HCl/Ethanol (25 mL conc.HCl in 100 mL EtOH) solution follow by 20 minutes centrifugation at 45 000 g by Beckman TM Allegra® 64R. The NPs were washed five times in the extraction solution for 2 hours under sonication. And, one last washing was performed in water.

Synthesis of Supported Lipid Bilayer(SLB) on Mesoporous Silica Nanoparticles (MSNPs).

Phospholipids were dissolved in chloroform/methanol 9:1 at a range of concentrations of 2 to 12 mg/mL. For SLB on MSNPs, the phospholipids ratio was DPPC/DOPS/cholesterol 75/20/50. And, for SLB$^{PEG}$ on MSNPs, the ratio was DPPC/DOPS/cholesterol/DSPE-PEG 75/20/50/10. The total volume of lipid mixture was 1 mL. Then, these lipids were evaporated to produce a lipid film. Four mL of MSNPs at 5 mg/mL were mixed with the lipid film. The suspension was ultra-sonicated with Ultrasonicator Sonics Vibra Cell® during 20 minutes at room temperature under argon flow at 29% of amplitude pulsed mode 10 s/10 s. The excess of liposomes was removed after centrifugation at 45 000 g by Beckman TM Allegra® 64R centrifuge. The SLB on MSNPs obtained were stored at 4° C. under argon.

Nanoparticles Characterization.

XRD Analysis.

The MSNPs and MSNPs+ samples were dried by lyophilization, to get 100 mg of powder. The silica nanomaterials were characterized by X-ray diffraction (XRD) in Brüker D8 Discover® HR XRD. The pore size was calculated by the Bragg's law: $n\lambda=2d \sin\theta$ (1) With n the order of diffraction (n=1), $\lambda$ the diffracted wavelength (i.e. copper X-Ray source, $\lambda$Copper=1.54), d the grating space between atomic lattice planes, and $\theta$ the angle between the incident beam and the scattering planes.

BET Experiments.

The MSNPs and MSNPs+ samples were evaporated by lyophilization, to get 100 mg of powder. The textural properties, including the BET (Brunauer-Emmett-Teller) specific surface area (SBET), specific pore volume (Vp) and pore diameter (Dp), were determined from low-temperature N2 adsorption-desorption measurements collected using an ASAP 2010 Micrometrics apparatus. Prior to the analysis, the samples were degased under vacuum at 150° C. until the static pressure was less than 6.6×10-4 Pa. The specific surface area was calculated from the N2 sorption isotherm using the BET equation and taking into account the cross-sectional area of a physically adsorbed N2 molecule (0.1620 nm2). The pore diameter and pore size distributions were calculated from the desorption branch of the isotherms using the Barrett-Joyner-Halenda (BJH) method.

DLS Analysis.

Malvern Nano Zetasizer® measure the size and Zeta potential of NPs by using dynamic light scattering size (DLS). The analysis was performed with 0.1 mg/mL for each sample.

NTA Analysis.

Nanoparticles Tracking Analysis (NTA) used a light scattering method which relates the rate of Brownian motion to particle size. This method allows direct and real time visualizing and analyzing of the NPs in liquids. During NTA measurement, NPs are illuminated by a focused laser beam and analyzed by the light scattered by each individual particle in the microscope onto the image sensor of a charge-coupled device (CCD) camera. The camera visualizes and records the frames of the particles in solution. The NTA software identifies and individually tracks the particles moving under Brownian motion. This measurement uses the temperature and the viscosity of the liquid to calculate particle size through the Stokes-Einstein equation. The Nanosight® analyses the particles with a size range from 30 to 1 µm. The samples were diluted at 0.01 mg/mL for analysis.

FT-IR Spectroscopy.

Each sample was mixed with KBr in a weight ratio of 1.5:100. Samples were ground for 2 minutes and then pressed into a pellet under 450 kg·cm-3. The spectra are performed with FTIR Bruker VERTEX 70 equipped with an MCT detector via an Attenuated Total Reflection (ATR), and KBr background is substracted.

Scanning Electron Microscopy (SEM) Analysis of Nanoparticles.

One drop of each silica sample (MSNPs+ and MSNPs) was deposited on a copper support and dried for 3 hours. Pictures were acquired on a FEI HELIOS NanoLab 650™ scanning electron microscopy working at 2 kV.

Transmission Electron Microscopy (TEM) Analysis of Nanoparticles.

To ensure the relevant dispersion of MSNPs, NanoPlus-Grids with a 15 nm Nitride monolayer were used as analysis support. One drop of each silica sample was deposited on a grid and fully dried before measurement. The shape, porosity and size of the nanoparticles were characterized by FEI Tecnai™ Transmission Electronic Microscopy (TEM) operating at 200 kV.

CryoTransmission Electron Microscopy (CRYO-TEM) Analysis of Nanoparticles.

The purpose of the CRYO-TEM analysis is to determine the presence of the lipid bilayer surrounding Silica NPs. The samples were frozen with liquid nitrogen in carbon grids by FEI tool™ for sample preparation. Analyses were performed using FEI Titan Krios™ CRYO-TEM operated at 200 kV.

LC-MS Experiments.

The LC-MS Thermo Scientific Dionex BIO LC system is coupled with the mass of LTQ Orbitrap Elite. The system consisted of a GS50 gradient pump, AS50 Auto Sampler with oven column of thermal compartment. The separation was performed at 40° C. on a GRACE visionHT C18 HL column (150×2.1 mm i.d., 3 μm) from Dionex Bio LC with the scan mass of 300 and 1 000. The flow rate was 0.25 mL/min for the mobile phases (mobile phase C, 5 mM ammonium acetate in water (pH 4.0) and mobile phase D, 5 mM ammonium acetate in methanol). The binary linear gradient began from a mixture of 20% C and 80% D and ended at 100% D. The SLB on MSNPs and SLB$^{PEG}$ on MSNPs samples were directly mixed in the solution of dichloromethane/methanol (9:1) to destabilize the lipid bilayer around the MSNPs. The NPs were removed by Beckman TM Allegra® 64R centrifuge, and the samples were diluted in methanol. The calibration range was performed in methanol with the concentration of lipid mixture 1, 10, 25, 50, 75 and 100 μg/mol. The sample injection volume was 50 μL. Data analysis was performed with the software ThermoXcalibur Qual Browser. The attenuation was ±6 ppm.

Hemolysis Assay.

The hemolysis assay was performed in two conditions, PBS buffer and human plasma. Human whole blood was freshly collected from healthy donors with their signed consent in a tube containing EDTA. The collection and use of healthy donor blood has been approved by the National Ethics Committee for Research of Luxembourg (CNER). Four mL of blood were diluted with 8 mL of Dulbecco's phosphate-buffered saline (PBS). Red blood cells (RBCs) were isolated by centrifugation at 2 500 g for 10 minutes and washed 3 times with PBS. Then, RBCs were diluted in 40 mL of PBS. The human plasma was collected after the first centrifugation of the blood. Nanoparticles were diluted in 0.8 mL of PBS or human plasma with a concentration of 125, 625 and 1 250 μg/mL and 0.2 mL of diluted RBCs were added to make a final concentration of 0.1, 0.5 and 1 mg/mL.

For the positive and negative control, 0.2 mL of RBCs were added in 0.8 mL of water or PBS/human plasma respectively. The solutions were briefly mixed and left at room temperature for 2 hours at static conditions. Then the solutions were briefly mixed and centrifuged at 2 500 g for 5 minutes. One hundred μL of each sample's supernatant were transferred into a 96-well plate. The RBCs suspension with silica materials was analyzed with the absorbance of hemoglobin at 540 nm with a reference wavelength of 640 nm (FluoSTAR Optima, BMG Labtech). The percentage of hemolysis was calculated using the formula: Hemolysis %=[(sample absorbance−negative control)/(positive control−negative control)]×100%. The experiment was repeated 4 times.

Use of the Negatively Charged Supported Lipid Bilayer (SLB) in the Biomimetism of Red Blood Cells (RBC)

Supported lipid bilayer (SLB) on mesoporous silica nanoparticles can be used as a nanovector for multiple applications (such as drug delivery, contrast agent for imaging). For this purposes, mesoporous silica can be used as a cargo while SLB adsorbed on porous silica play the role of gate keepers.

One of the main drawbacks of this system is the colloidal stability when MSNPs, used as substrate for supported lipid bilayer, are close or below 70 nm. The curvature of such small MSNPs as well as the influence of their anionic charge impact the lipid bilayer coverage and can lead to defect in the lipid bilayer or/and inter-particulate aggregations.

To circumvent this, several reports propose the use of synthetic cationic lipids (such as DOTAP) to stabilize the lipid coating on silica and/or the use of pegylated phospholipid such as pegylated 1,2-distearoyl-sn-glycero-3-phosphoethanolamine (DSPE). Cationic supported lipid bilayers are quickly removed from the blood circulation and can induce immune toxicity as well as cell membrane defect. Pegylated lipid bilayers such as pegylated liposomes are suspected to induce CARPA (complement activation-related pseudoallergy) or other immune reaction after multiple injection.

The solution proposed by the present invention is to adsorb, on small cationic mesoporous silica, biomimetic supported lipid bilayer which mimics the phosphatidyl serine asymmetry as well as the charge of the red blood cells membrane. For this purpose, highly aminated mesoporous silica are coated during ultra-sonication process at room temperature by a supported lipid bilayer constituted by a range of 33% of cholesterol, 13.5% of DOPS, and 53.5% of DPPC (see below table II, line 4).

Table II thus shows the impact of the lipid formulation on the colloidal stability:

TABLE II

Influence of the lipid ingredients in regards of the colloidal stability of SLB@MSNPs formulated by ultra-sonication (US).

| Ingredients of the SLB | MSNPs used | Colloïdal stability after US | Size (NTA analysis) after US |
|---|---|---|---|
| DPPC: 80%/DOPS: 20% | MSNP + 55 nm | High aggregation | 240 ± 95.6 nm |
| DPPC: 72%/DOPS: 18%/Myrj S40: 10% | MSNP + 55 nm | Few aggregates | 152 ± 53.6 nm |
| DPPC: 53.5%/DOPS: 13.5%/Cholesterol: 33% | MSNP + 55 nm | No aggregation | 138 ± 43 nm |
| DPPC: 45.6%/DOPS: 11.5%/Cholesterol: 33%/Myrj S40: 10% | MSNP + 55 nm | Few aggregates | 177 ± 100 nm |
| DPPC: 80%/DOTAP: 20% | MSNP 55 nm | High aggregation | 239 ± 106 nm |
| DPPC: 53.5%/DOTAP: 11.5%/Cholesterol: 33% | MSNP 55 nm | High aggregation | 340 ± 134 nm |

TABLE II-continued

Influence of the lipid ingredients in regards of the colloidal stability of SLB@MSNPs formulated by ultra-sonication (US).

| Ingredients of the SLB | MSNPs used | Colloïdal stability after US | Size (NTA analysis) after US |
|---|---|---|---|
| DPPC: 72%/DOTAP: 18%/Myrj S40: 10% | MSNP 55 nm | High aggregation | 203 ± 75 nm |
| DPPC: 45.6%/DOTAP: 11.5%/Cholesterol: 33%/Myrj S40: 10% | MSNP 55 nm | Few aggregates | 194 ± 68 nm |

These ratios are equivalent to the ratio used for the synthesis of the MSNPs incorporated with SLB, as described in table I of the present invention (34% of cholesterol, 14% of DOPS and 52% of DPPC).

The number of equivalents of cholesterol relative to one equivalent of DOPS are thus comprised between 2.30 and 2.70, this number being in various instances equal to 2.50.

The strong cationic charges of the silica surfaces attract DOPS into the inner leaflet of the supported lipid bilayer resulting into DOPS asymmetric supported lipid bilayer in a similar way as RBC membranes.

The global charges are anionic as for RBC membranes.

For this particular purposes, ultra-sonication is required to suppress nanoparticle aggregation which appears when highly aminated mesoporous silica and DOPS liposomes are in contact without adding ultra-sonication or any other sources of energy. The rate of DOPS/Chol/DPPC has been designed to reach a strong degree of SLB stability to coat the mesoporous silica without any defects which induce holes in SLB as well as nanoparticles aggregation. These "aniocells" nanoparticles have a very low avidity for plasma proteins (similar to pegylated supported lipid bilayer), are non-toxic regarding blood cells (i.e. peripheral blood mononuclear cell (PBMC) and/or RBC) and keep good colloidal stability, even in blood plasma. The defect-free structure of the proposed supported lipid bilayer allows slowing down the diffusion of active ingredients loaded into the mesoporous silica (gate keepers activity). These specific properties result from the process of fabrication as well as the lipid composition selected to have biomimetic membrane.

The adsorption of plasma proteins on the silica surface forms a protein corona around NPs. To investigate the anti-biofouling properties of MSNP+@SLB−, the amount of proteins bound to the surface of NP have been determined (FIG. 28).

Remarkably, MSNP+@SLB− and MSNP+@SLB−/PEG exhibit fivefold less protein adsorption on their surfaces compared to bare MSNP.

SLB− acts like an anti-biofouling layer decreasing non-specific binding of proteins similar to the DSPE-PEG functionalized lipids. This antifouling property suggests therefore a different behavior of SLB− compared to a classical liposome. These results show that SLB− would improve the stability of MSNP in blood and might decrease unwanted phagocytosis by the reticuloendothelial system (RES).

The invention claimed is:

1. A negatively charged supported lipid bilayer on a positively charged surface of a mesoporous silica nanoparticle, the negatively charged supported lipid bilayer comprising cholesterol, 1,2-dioleoyl-sn-glycero-3-phospho-L-serine alias DOPS at the inner side of said lipid bilayer, and at least one lipid different from DOPS and cholesterol at the outer side of said lipid bilayer, wherein the number of equivalents of cholesterol relative to one equivalent of DOPS is comprised between 2.30 and 2.70, and in that the ζ-potential measured in milliQ water at a pH of 5.8 is inferior to −50 mV, wherein the mesoporous silica nanoparticle is completely surrounded by the negatively charged supported lipid bilayer, and wherein said supported lipid bilayer is a DOPS asymmetric supported lipid bilayer with regard to the distribution of at least one lipid different from DOPS and cholesterol, and
wherein the supported lipid bilayer further comprises 1,2-distearoyl-sn-glycero-3-phosphoethanolamine-N-amino(polyethylene glycol) 2 KDa alias DSPE-PEG (2000).

2. The negatively charged supported lipid bilayer on a positively charged mesoporous silica nanoparticle according to claim 1, wherein the at least one lipid different from DOPS and cholesterol is 1,2-dipalmitoyl-sn-glycero-3-phospholine alias DPPC.

3. The negatively charged supported lipid bilayer on a positively charged mesoporous silica nanoparticle according to claim 2, wherein the number of equivalents of the DPPC relative to one equivalent of the DOPS is comprised between 3.55 and 3.95.

4. The negatively charged supported lipid bilayer on a positively charged mesoporous silica nanoparticle according claim 1, wherein the positively charged mesoporous silica nanoparticle comprises at least one silica precursor and at least one organotriethoxysilane, the portion of the organotriethoxysilane to the silica precursor being comprised between 5% and 15%.

5. The negatively charged supported lipid bilayer on a positively charged mesoporous silica nanoparticle according to claim 1, wherein the cationic charges of the positively charged mesoporous silica nanoparticle are located at the silica outer surface compared to the silica inner surface.

6. A composition adapted for drug delivery comprising
a) a negatively charged supported lipid bilayer on a positively charged mesoporous silica nanoparticle, the negatively charged supported lipid bilayer comprising cholesterol, 1,2-dioleoyl-sn-glycero-3-phospho-L-serine alias DOPS at the inner side of said lipid bilayer, and at least one lipid different from DOPS and cholesterol at the outer side of said lipid bilayer, wherein the number of equivalents of cholesterol relative to one equivalent of DOPS is comprised between 2.30 and 2.70, and in that the ζ-potential measured in milliQ water at a pH of 5.8 is inferior to −50 mV, wherein the mesoporous silica nanoparticle is completely surrounded by the negatively charged supported lipid bilayer, and wherein said supported lipid bilayer is a DOPS asymmetric supported lipid bilayer with regard to the distribution of at least one lipid different from DOPS and cholesterol, and wherein the supported lipid bilayer further comprises 1,2-distearoyl-sn-glycero-3- phosphoethanolamine-N-amino(polyethylene glycol) 2 KDa alias DSPE-PEG (2000); and b) at least one active moiety, wherein, the at least one active moiety is a molecule presenting anticancerous properties, or the at least one active moiety is a contrasting agent, or the at least one active moiety is a cosmetic agent.

7. The composition according to claim 6, wherein the molecule presenting anticancerous properties is chosen among the following list: doxorubicin, paclitaxel, docetaxel, any mitotic inhibitor, cisplatin, 5-FU, temozolomide.

8. The composition according to claim 6, wherein the contrasting agent is any gadolinium derivative, any iodine derivative, any gold derivative, indocyanine green, rhodamine, fluorescein, methylene blue, 5-aminolevulinic acid, any porphyrin precursor.

9. The composition according to claim 6, wherein the cosmetic agent is retinoic acid, vitamin E, nicotinic acid, ascorbic acid, any B vitamin, any antioxidant.

10. The composition in accordance with claim 6, wherein use of the negatively charged supported lipid bilayer on a positively charged mesoporous silica nanoparticle as biomimetic compound configured to mimic at least one of the membrane asymmetry and the electrical conductivity of a red blood cell.

* * * * *